US008903501B2

(12) United States Patent
Perryman

(10) Patent No.: US 8,903,501 B2
(45) Date of Patent: Dec. 2, 2014

(54) METHOD, SYSTEM AND APPARATUS FOR CONTROL OF PANCREATIC BETA CELL FUNCTION TO IMPROVE GLUCOSE HOMEOSTASIS AND INSULIN PRODUCTION

(75) Inventor: Laura Tyler Perryman, Scottsdale, AZ (US)

(73) Assignee: Neural Diabetes, Miami Beach, FL (US)

( * ) Notice: Subject to any disclaimer, the term of this patent is extended or adjusted under 35 U.S.C. 154(b) by 0 days.

(21) Appl. No.: 13/436,293

(22) Filed: Mar. 30, 2012

(65) Prior Publication Data
US 2012/0303098 A1 Nov. 29, 2012

Related U.S. Application Data

(63) Continuation-in-part of application No. PCT/US2011/065653, filed on Dec. 16, 2011.

(60) Provisional application No. 61/424,546, filed on Dec. 17, 2010.

(51) Int. Cl.
A61N 1/36 (2006.01)

(52) U.S. Cl.
CPC ........ *A61N 1/36057* (2013.01); *A61N 1/36121* (2013.01)
USPC .......................................................... 607/62

(58) Field of Classification Search
USPC .......................................... 607/62, 116–118
See application file for complete search history.

(56) References Cited

U.S. PATENT DOCUMENTS

| | | | |
|---|---|---|---|
| 7,502,649 B2* | 3/2009 | Ben-Haim et al. | 607/40 |
| 8,116,883 B2* | 2/2012 | Williams et al. | 607/120 |
| 8,321,012 B2* | 11/2012 | Della Rocca et al. | 607/3 |
| 2003/0055464 A1* | 3/2003 | Darvish et al. | 607/40 |
| 2004/0016590 A1* | 1/2004 | Iwano | 180/443 |
| 2004/0162590 A1* | 8/2004 | Whitehurst et al. | 607/17 |
| 2004/0172075 A1* | 9/2004 | Shafer et al. | 607/9 |
| 2005/0055065 A1* | 3/2005 | Campbell | 607/46 |
| 2006/0111754 A1* | 5/2006 | Rezai et al. | 607/41 |
| 2007/0016262 A1 | 1/2007 | Gross et al. | |
| 2007/0027484 A1* | 2/2007 | Guzman et al. | 607/2 |
| 2007/0027514 A1* | 2/2007 | Gerber | 607/116 |
| 2009/0210041 A1* | 8/2009 | Kim et al. | 607/117 |
| 2009/0312255 A1 | 12/2009 | Dosch et al. | |
| 2010/0036451 A1* | 2/2010 | Hoffer | 607/42 |

OTHER PUBLICATIONS

PCT/US2011/065653—International Search Report and Written Opinion—mailed Apr. 19, 2012.
Holzer et al., "Dissociation of Dorsal Root Ganglion Neurons into Afferent and Efferent-like Neurons," Neuroscience, vol. 86, No. 2, 1998, pp. 389-398.
Sann et al., "Efferent Functions of C-fiber Nociceptors," Z. Rheumatol, vol. 57, Suppl 2, 1988, pp. 8-13.

* cited by examiner

*Primary Examiner* — Paula J Stice
(74) *Attorney, Agent, or Firm* — Fish & Richardson P.C.

(57) ABSTRACT

The present invention provides methods, systems and apparatuses for effecting excitation or inhibition of small sensory nerve fibers, such as C-afferent fibers, by electrical stimulation of nerves innervating the pancreas in diabetic subjects. In an aspect the methods are directed to effecting insulin production and for the treatment of diabetes. This invention includes a closed or open loop feedback control system in which biomarker levels are monitored in order to direct electrical stimulation. An implantable or external neural stimulation device is also provided.

41 Claims, 11 Drawing Sheets

METHOD, SYSTEM AND APPARATUS FOR CONTROL OF PANCREATIC BETA CELL FUNCTION TO IMPROVE GLUCOSE HOMEOSTASIS AND INSULIN PRODUCTION

CROSS REFERENCE TO RELATED APPLICATIONS

This application claims benefit of U.S. provisional Patent Application 61/424,546, filed 17 Dec. 2010, and is a continuation-in-part of co-pending International Patent Application No. PCT/US2011/065653, filed 16 Dec. 2011, the disclosures of both of which are hereby incorporated by reference in their entirety.

BACKGROUND OF INVENTION

The past quarter century has witnessed a dramatic increase in the prevalence in subjects of a cluster of inter-related metabolic disease states, primarily caused by obesity and immune disease states, jeopardizing homeostasis and leading to the diabetic state. The incidence of diabetes, with or without obesity, has reached epidemic proportions, bringing with it impaired quality of life and life span due to serious clinical co-morbidities such as peripheral vascular and neuropathic disease, with or without pain, ulcerative skin lesions often leading to infection, gangrene, and amputation, vision loss, cardiac and renal failure and brain disorders. Without question, chronic disease associated with diabetes represents a heavy and growing burden to society in terms of both direct healthcare costs that have reached catastrophic levels and mortality rates (American Health Rankings, 2010 edition).

According to American Diabetes Association, as of 2010, 23.6 million children and adults, approximately 8% of population in the United States (US) have diabetes, and over 57 million people are clinically considered pre-diabetic in the US. According to United HealthCare, based on current trends, 52% of the US adult population could have pre-diabetes or diabetes by 2020—up from an estimated 40% in 2010, resulting in costs estimated at $3.4 trillion for diabetes-related care over the decade from 2010 to 2020. The incidence of adolescent type 2 diabetes (T2D) has increased 10 fold from 1982 to 1994 (Pinhas-Hamiel 1996). Over 25% of obese children are considered glucose intolerant. Insulin resistance is related to inflammation and obesity induces a state of chronic inflammation. In obese states, adipose tissue secretes inflammatory agents such as cytokines Adipose tissue macrophages alter insulin sensitivity in animal models. Obesity can be reframed as an inflammatory disease, with macrophages acting at the junction between over nutrition and inflammation.

Insulin is a peptide hormone produced by beta cells ($\beta$-cells) within the islets of Langerhans in the endocrine pancreas. Insulin promotes glucose utilization, protein synthesis, and the formation and storage of neutral lipids. Insulin is generally required for the entry of glucose into muscle. Glucose stimulates both the secretion and biosynthesis of insulin. Basal insulin secretion is normally generated to synthesize glycogen from glucose in the absence of glucose-stimulated insulin secretion.

Insulin and related insulin-like growth factors (IGF-1) give trophic support to neural tissue; their receptors are present on vanilloid transient receptor potential 1 (TRPV1) neurons, which are essential in serving to maintain neural vitality and to promoting regeneration of small sensory nerve fibers (Migdalis 1995; Sathianathan 2003; VanBuren 2005). Moreover, TRPV1 sensory neurons appear to be down regulated in pre- and post-diabetic states whereby they may fail to influence the appropriate release of calcitonin gene-related peptide (CGRP) and other neuropeptides that influence production of insulin from the beta cell (Okabayashi 1989). Reports of preclinical and clinical experiments state that exogenous administration of CGRP or induction of the endogenous release of CGRP from TRPV1 sensory neurons by the application of a TRPV1 antagonist results in the following relevant biological responses: (1) pain signals conveyed to the central nervous system (CNS); (2) a neurogenic inflammatory response consisting of vasodilatation and edema formation, the latter not pronounced in humans; (3) insulin secretion at appropriate concentrations and (4) immunosuppression (Nagy 2004, Brain and Grant 2004; Razavi 2006). In animal models of Type I diabetes (T1D) with insulinopenia, targeted expression of CGRP to $\beta$-cells or local intra-arterial administration of substance P (SP), which is co-localized with CGRP in TRPV1 sensory neurons but not as prevalent, has been reported to prevent or ameliorate diabetes (Khachatryan 1997; Razavi 2006).

In addition to T1D, $\beta$-cell dysfunction with impaired insulin regulation is also observed in subjects in the early stages of diabetes development, including impaired glucose tolerance (IGT) and obesity-related hyperinsulinemia. In obese animals, capsaicin-sensitive C-fibers containing TRPV1 sensory neurons are markedly impaired, suggesting that intra-pancreatic neuronal release of CGRP is reduced, which would further amplify $\beta$-cell dysfunction particularly if the pancreas is maladapted to high levels of insulin (Ahren 2009). Paradoxically, the deletion or degeneration of TRPV1 sensory neurons innervating the pancreas has been reported to result in improved glucose homeostasis and insulin production (Razavi 2006; Gram 2007).

Impaired CGRP release due to TRPV1 sensory neuron pathology and/or abnormal interaction in the pathway featuring insulin production and the feedback function of the insulin receptor exhibit an inflammatory (e.g. autoimmune) state and are seen in T1D. It has been reported that increased concentrations of CGRP and other neuropeptides can prevent T1D in experimental animal models (Khachatryan 1997).

The release of CGRP to the $\beta$-cell has been reported to improve glucose and insulin homeostasis (see Gram 2005, 2007). Animal experiments have reported that sensory nerve dysfunction may contribute to hyperinsulinism, pre-diabetes initiation and progression of diabetes (Carillo 2005; Leighton and Foot 1995). Reports indicate that an imbalance in the insulin feedback control system may be "normalized" through enhancing the local supply of sufficient neuropeptides, including CGRP (Razavi 2006, Khachatryan 1997). Ablation and administration of TRPV1 antagonists have been reported to improve glucose and insulin homeostasis in subjects with pre-diabetes or T2D. See Dosch et al., U.S. patent application Ser. No. 12/478,898, incorporated by reference in its entirety.

TRPV1 sensory neurons have been shown to act as a central controller of both $\beta$-cell stress and T cell infiltration (Dosch et. al). Elimination of neurons containing TRPV1 by capsaicin or resiniferatoxin (RTX) or transection of sensory nerves innervating the pancreas and functional normalization of TRPV1 sensory neurons has the same net islet-specific outcomes: prevention of diabetes, improved glucose/insulin homeostasis, normalized insulin sensitivity and abrogation of insulitis or T1D (Szallasi 1999).

Systemic delivery of pharmaceutical agents has been the typical treatment for $\beta$-cell dysfunction and the hyperglycemia associated with diabetes; nevertheless, this approach can have limited dosing and compliance issues, and serious side effects. While non-insulin and insulin pharmacotherapies have been the hallmark in controlling hyperglycemia, there are no therapies that induce immunosuppression, and prevent/attenuate diabetes without significant risk.

SUMMARY OF THE INVENTION

Figure 1:
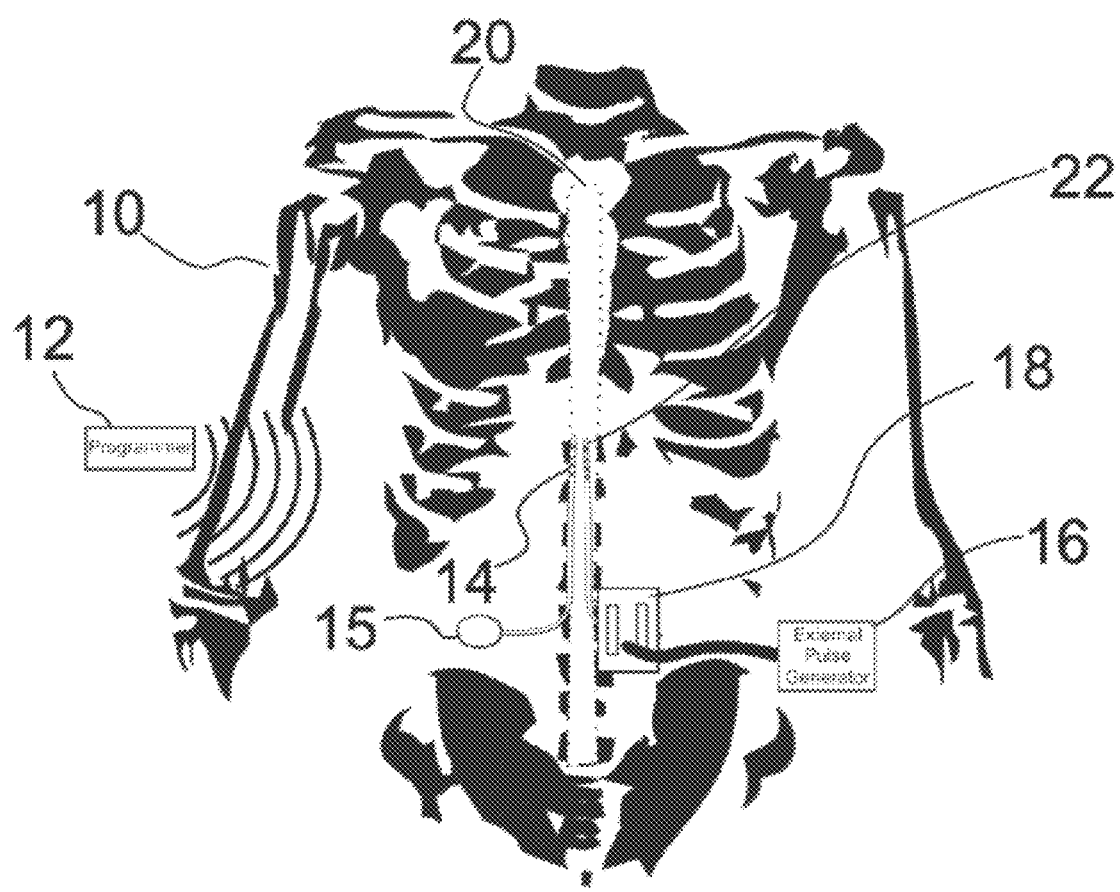
FIG. 1 shows a diagram of a schematic view of a diabetic subject (1) with an implanted neural stimulation electrode lead (22) to stimulate the targeted sensory nerves through epidural spinal cord (20) stimulation. Also shown is the option for a receiver (16) at the end of the electrode lead and a typical wireless pulse generator comprising a programmer (12), a cable (14) and a antenna (18).

Provided herein are methods, systems and apparatuses for preserving, restoring or affecting pancreatic beta cell function in a subject. These methods include electrically stimulating C-afferent sensory nerve fibers innervating pancreatic beta cells in the diabetic subject, in which the electrical stimulation serves to modulate a secretion of calcitonin gene-related peptide (CGRP) from the C-afferent sensory nerve fibers; determining a level of a biomarker in the subject and repeating the electrical stimulation as a function of the level of the biomarker.

The methods, systems and apparatuses include electrical stimulation carried out via one or more electrodes or pairs thereof. The one or more electrodes or pairs thereof can be contained in an implantable lead that is positioned in the subject proximal to nerve tissue to be stimulated, including one or more leads positioned proximal to epidural spinal cord column at any vertebral segment from T7 to L1, dorsal root or dorsal root entry zone at any vertebral segment from T7 to L1, spinal nerve bundles leaving at any vertebral segment from T7 to L1, dorsal root ganglia bundles leaving at any vertebral segment from T7 to L1, peripheral nerves innervating endocrine pancreas beta cells, abdominal nerves or their cutaneous branches, a surface of endocrine pancreas, or combinations thereof. The one or more electrodes or pairs thereof or one or more leads are placed ipsilaterally or bilaterally. The electrical stimulation is carried out simultaneously or sequentially.

The methods, systems and apparatuses include electrical stimulation that is effected wirelessly. For example, the electrical stimulation is effected using a wirelessly powered and controlled implanted lead.

The methods, systems and apparatuses include electrical stimulation that is carried out at the following parameters: a pulse width from 20 μsec to 1 ms, a frequency from 1 Hertz (Hz) to 10,000 Hz, and power amplitude from 0.2 to 14 Volts (V) or 0.1 to 20 milliamps (mA). The frequency of the electrical stimulation is between 5 and 10,000 Hz. The frequency of said electrical stimulation is between 1 and 50 Hz resulting in enhancement of secretion and, optionally, the pulse width is in the range of 200 to about 450 microseconds. The frequency of the electrical stimulation is between 60 and 10,000 Hz resulting in the inhibition of the secretion and, optionally, the pulse width is in the range of about 450 to about 1000 microseconds.

The methods are directed to a subject who suffers from beta cell dysfunction or impairment from diabetes mellitus states, specifically T1D, T2D, or diabetes insipidus.

The methods are performed in which the subject needs not adopt a lifestyle change.

The methods are performed in which the subject effects the step of repeating the electrical stimulation as a function of the level of a biomarker or where the step can be effected automatically. The biomarker includes, but is not limited to, any one or more of insulin, glucose, CGRP, abdominal skin blood flow, abdominal skin temperature and abdominal muscle activity. Other biomarkers may include, but are not limited to, H1Ac and inflammatory cytokines.

The method is performed in which the biomarker is insulin and the subject is a male subject and the level is below about 8.8 μIU/mL or the subject is a female subject and the level is below about 8.4 μIU/mL; and the electrical stimulation is carried out to excite the C-afferent sensory nerve fibers innervating pancreatic beta cells. The method is performed in which the biomarker is insulin and the subject is a male subject and the level is above about 8.8 μIU/mL or the subject is a female subject and the level is above about 8.4 μIU/mL; and said electrical stimulation is carried out to inhibit the C-afferent sensory nerve fibers innervating pancreatic beta cells. The method is performed in which the biomarker is glucose and the level is above about 120 mg/dL and the electrical stimulation is carried out to excite the C-afferent sensory nerve fibers innervating pancreatic beta cells. The method is performed in which the biomarker is glucose and the level is below about 100 mg/dL and the electrical stimulation is carried out to inhibit said C-afferent sensory nerve fibers innervating pancreatic beta cells.

A system is provided for preserving, restoring, or affecting pancreatic beta cell function in a subject, comprising: means for detecting a biomarker level; means for producing electrical stimulation as a function of the biomarker level; and means for applying the electrical stimulation to stimulate C-afferent sensory nerve fibers innervating pancreatic beta cells in a subject, in which said electrical stimulation modulates a secretion of calcitonin gene-related peptide (CGRP) from said C-afferent sensory nerve fibers. The means for applying the electrical stimulation may be positioned at or near dorsal root ganglion, splenic nerve, or dorsal column. The means for producing may perform electrical stimulation in an open loop format and at predetermined intervals. Preferably the means for producing performs electrical stimulation in a manner to maintain hormone levels at a predetermined concentration. The open loop format may include alerting the subject to a change in glucose homeostasis. The subject may also be alerted when the biomarker level achieves a threshold level. Accordingly the electrical stimulation may be initiated by the subject.

Alternatively the means for producing may perform electrical stimulation in a closed loop format. Preferably, the means for producing compares detected biomarker levels to at least one predetermined range, and the means for detecting transmits information about the biomarker level to the means for producing. As well the means for producing may be further configured to initiate adjustments to parameter settings of the electrical stimulation, to evaluate the efficacy of the electrical stimulation so that the parameter settings can be adjusted, or to compare the biomarker level to an historic or normative level and adjusts the electrical stimulation based on the comparison. Various aspects of the system may be implantable in the subject, including but not limited to the means for applying or the means for producing. The system may further comprise a means for receiving incoming signals from an external programmer. The means for producing preferably electrically processes the incoming signals and produces the electrical stimulation sequentially without the aid of a battery. Moreover the electrical stimulation is preferably charge-balanced and is effected automatically.

An apparatus is likewise provided for preserving, restoring, or affecting pancreatic beta cell function in a subject, comprising: a sensor that detects a biomarker level; a pulse generator to produce electrical stimulation as a function of the biomarker level; and an electrode lead or a multiple electrode lead array; in which the pulse generator applies the electrical stimulation to the electrode lead or multiple electrode lead array; in which the electrode lead or multiple electrode lead array comprises an electrode for applying the electrical stimulation to stimulate C-afferent sensory nerve fibers innervating pancreatic beta cells in a subject, in which the electrical stimulation modulates a secretion of CGRP from said C-afferent sensory nerve fibers. Preferably the electrode lead or multiple electrode lead array is positioned at or near dorsal root ganglion, splenic nerve, or dorsal column and is implantable in the subject, along with the pulse generator.

The apparatus may further comprise a radio frequency antenna for receiving incoming signals from an external programmer. Preferably the pulse generator electrically processes the incoming signals and produces the electrical stimulation sequentially without the aid of a battery.

"C-afferent sensory nerve fibers" means unmyelinated postganglionic fibers of the autonomic nervous system, also the unmyelinated fibers at the dorsal roots and at free nerve endings, that convey sensory impulses from the periphery to the central nervous system.

"Subject" means any animal, such as a human, with an insulin-producing organ, such as an endocrine pancreas, who is diabetic.

"Pancreatic beta cells" means insulin-producing cells situated in the islets of Langerhans.

"Electrical stimulation" means the application of electrical current to stimulate nerves.

"Biomarker" means any physiological indicating species produced by a diabetic subject. Examples of biomarkers include, but are not limited to, insulin, glucose, CGRP, abdominal skin blood flow, abdominal skin temperature, and abdominal muscle electrical activity.

"Electrode" means an electrical conductor used to make contact with a nonmetallic part of a circuit. An electrode can be an anode or a cathode. An electrode pair means two electrodes: one anode and one cathode. Configurations of multiple electrodes can be multiple electrode pairs or one or more anode or cathode with any number of electrodes of the reverse polarity.

"Epidural spinal cord column" means the space superficial to the dura matter that exists between it and the internal surfaces of the vertebral bones and their supporting ligamentous structures of the spine.

"Dorsal root or dorsal root entry zone" means the posterior root that is the afferent sensory root of a spinal nerve.

"Dorsal ganglia" means the nerve structure at the distal end of the dorsal root, which contains the neuron cell bodies of the nerve fibers conveyed by the root.

"Spinal nerve bundles" means nerves within the spinal cord, which are grouped together.

"Peripheral nerves" means nerves and ganglia outside of the brain and spinal cord.

"Diabetes mellitus" means diabetic states that include T1D, T2D and gestational diabetes.

"Type I diabetes (T1D)" means a condition characterized by loss of the insulin-producing beta cells of the islets of Langerhans in the pancreas leading to insulin deficiency. This type of diabetes can be further classified as immune-mediated or idiopathic. T1D can affect children or adults but was traditionally termed "juvenile diabetes" because it represents a majority of the diabetes cases in children.

"Diabetes insipidus" means a condition characterized by excessive thirst and excretion of large amounts of severely diluted urine, with reduction of fluid intake having no effect on the latter.

"Type II diabetes (T2D)" means a condition characterized by insulin resistance, which may be combined with relatively reduced insulin secretion.

"Lifestyle change" means changes in diet, exercise, nutraceutical and pharmaceutical regimens.

DETAILED DESCRIPTION OF THE EMBODIMENTS

Provided herein are methods, systems and apparatuses to provide electrical neural stimulation of neurons containing the vanilloid transient receptor potential 1 (TRPV1) receptor, small sensory nerve fibers of other TRPV sub-families, and autonomic nerve fibers to control the production of insulin from endocrine pancreatic beta cells. The disclosed embodiments are related to the excitation or inhibition of the small sensory nerves, preferentially C-afferent fibers, by electrical neural stimulation of the nerve fibers that innervate the endocrine pancreas and act upon pancreatic beta cells. Such methods, systems and apparatuses can be used to treat subjects with various diabetic states. Embodiments of the invention allow stimulation of neurons containing the TRPV1 receptor, many of which release a neuropeptide, calcitonin gene-related peptide (CGRP), which in turn influences the production of insulin from pancreatic beta cells. Embodiments of the invention further include a closed or open loop feedback control system in which biomarker levels are monitored and used to regulate the applied neural stimulation. Embodiments of the invention also include an implantable or external neural stimulation device.

While not wishing to be held by theory, embodiments of the invention are based on observations that electrical stimulation of the dorsal root ganglia sensory nerve fiber bundles reverses insulin resistance. Thus, in insulinopenic states, purportedly due to immune and/or endocrine dysfunction and associated with down-regulation of insulin receptors, CGRP (with SP) release induced by electrical stimulation of specific neural tissue can serve as insulin "replacement therapy." CGRP can therefore be used therapeutically in terms of improving the local immunoregulatory state of the endocrine pancreas, pancreatic neurogenic vasodilatation (blood flow) and balancing an abnormal functional circuit comprised of low insulin production-low activation of TRPV1 sensory neurons-low release of CGRP. This concept also supports a view of a neuro-immune-endocrine link in β-cell function and the role for insulin-responsive TRPV1 sensory neurons in β-cell function and diabetes pathoetiology.

Consequently, there appears to be a local feedback interaction between β-cells and the TRPV1 sensory neurons innervating the islets with nerve terminals responding to insulin by release of neuropeptides that sustain β-cell physiology in an optimal range. Normally this interaction is in "balance" but in T1D animal models, as well as in T2D models, hypofunction of TRPV1 unbalances the feedback, with β-cell stress due to hyperinsulinism, insulin resistance, and infiltration by T-cell pools independently generated. Removing TRPV1 sensory neurons (e.g., desensitization) leads to elimination of the unbalanced pathogenic interaction whereas administering neuropeptides exogenously (or by sensitization of TRPV1 neurons) may renormalize the interaction. Consequently, suppressed neuropeptide release due to impaired TRPV1 sensory neurons and/or to abnormal β-cell function including down-regulation of insulin receptors on TRPV1 sensory neurons can be addressed by two approaches. One approach is the desensitization, removal or inhibition of TRPV1 sensory neurons. Another approach is the sensitization or excitation of TRPV1 sensory neurons. Both treatment options can re-balance the interaction between the β-cell and the TRPV1 sensory neuron depending on the state of the subject's disease state. Further, improved local insulin production induced by release of CGRP from TRPV1 sensory neurons can restore function of the normalized feedback and glucose-insulin homeostasis by promoting insulinotrophic action on sensory nerves in diabetic subjects where production of insulin is severely impaired.

Embodiments of the invention include the control of glucose homeostasis by stimulation of TRPV1 sensory neurons that innervate the endocrine pancreas. Electrical neural stimulation can be performed by directing the electrical stimulation at one or more anatomical sites including, but not limited to, 1) epidural spinal cord column, which can include the area at vertebrae segments T7 to L1 (and can include branches that innervate the endocrine pancreas beta cells); 2) dorsal root and dorsal root entry zone, which can include the area at vertebrae segments T7 to L1; 3) spinal nerve bundles, which can include the area leaving the vertebrae segments T7 to L1; 4) dorsal root ganglia bundles, which can include the area leaving the vertebrae segments T7 to L1; 5) peripheral nerves, such as the splenic nerve which innervate the endocrine pancreas beta cells; 6) abdominal nerves or their cutaneous branches (which can be stimulated by TENS or other external stimulation); and 7) directly at the surface of the endocrine pancreas. Electrical neural stimulation may be in more than one area simultaneously or sequentially, ipsilaterally, or bilaterally.

While not wishing to be held by theory, in an aspect embodiments of the invention are directed to methods, systems and apparatuses that activate/deactivate TRPV1 sensory neurons associated with pancreatic beta cell function by using charge-balanced voltage or current controlled electrical pulses originating from the electrical neural stimulation volume conduction of electrode leads. The TRPV1 sensory neuron can be stimulated at a frequency range from 1-10 Hz, 1-20 Hz, or 1 to 50 Hz. This frequency range often results in excitation of the TRPV1 sensory neurons. Such excitation can increase β-cell activity and promote insulin release. The preferred frequency for neural excitation can be 5 Hz. For inhibition of the TRPV1 sensory neuron, which can mimic the effects of ablation or receptor blocking, a frequency of 60 Hz or greater can be applied. Such inhibition can balance the insulin-dependent TRPV1 neuronal feedback system, thereby increasing insulin release. The frequency range for neural inhibition can be from 60 to 10,000 Hz. The preferred frequency for neural inhibition can be 100 Hz.

These and other electrical stimulation parameters used to stimulate TRPV1 sensory neurons can differ from those commonly used clinically for control of inflammatory and neuropathic pain and peripheral vascular disease. Stimulation parameters, in addition to frequency, that can be modulated include, but are not limited to, duty cycle, duration, waveform shape, amplitude, voltage, and magnitude. In an embodiment, the pulse width is in the range of 20 microseconds (μsec) to 1 millisecond (ms). The pulse width can be 250 μsec to 450 μsec, which can result in excitation of the TRPV1 sensory neuron. The pulse widths can be 500 μsec to 1 ms, which can result in inhibition of the sensory neuron. The power amplitudes can be from 0.2 to 14 Volts, or 0.1 to 20 mA, depending on whether the power is voltage or current-driven.

In another embodiment of the invention, one or more biomarker levels in the subject are monitored and the information resulting from such monitoring is used to determine subsequent delivery of electrical stimulation. The biomarker can be insulin or glucose. Normal levels of insulin are about 8.8 μIU/mL in male subjects and about 8.8 μIU/mL in female subjects. Normal levels of blood glucose are about 100-120 mg/dL. Consequently, in certain embodiments of the invention, the C-afferent sensory nerve fibers innervating pancreatic beta cells are either excited or inhibited to promote glucose homeostasis in response to abnormal biomarker levels. The biomarker can also be abdominal skin blood flow, abdominal skin temperature, or abdominal muscle electrical activity measured by sensors. Abdominal muscle electrical activity can be monitored by electromyography (EMG). Subsequent delivery of electrical stimulation can be performed by open loop control, whereby the subject is notified to begin, end or adjust parameters of the stimulation. Subsequent delivery of electrical stimulation can be performed by closed loop control, by an apparatus comparing sensed physiological values to historic or normative values, and automatically adjusting the stimulation output accordingly.

In embodiments of the invention, the methods, systems and apparatuses disclosed herein are used to protect the endocrine pancreas against abnormal immune-cell accumulation or inflammation (insulitis, i.e., T1D). Impaired CGRP release due to TRPV1 sensory neuron pathology and/or abnormal interaction in the pathway featuring insulin production/insulin receptor function and CGRP release favor an inflammatory state and, hence, T1D becomes a model of immune dysregulation, due to the early onset of sensory nerve impairment leading to inflammatory destruction of insulin-producing β-cells and to insulin deficiency and hyperglycemia. Increased concentrations of neuropeptides like CGRP have been shown to prevent T1D in experimental animal models (Ahren, 2000). Endogenous produced CGRP is therefore used therapeutically in terms of improving the local immunoregulatory state of the endocrine pancreas, pancreatic neurogenic vasodilatation (blood flow) and balancing an abnormal functional circuit comprised of low insulin production-low activation of TRPV1 sensory neurons-low release of CGRP.

In embodiments of the invention, the methods, systems and apparatuses disclosed herein are used for the treatment of diabetes. Sensitization of TRPV1 neurons stimulates insulin action and improves glucose and insulin homeostasis. Consequently, in various embodiments, T1D, T2D, diabetes mellitus, diabetes, diabetes insipidus and beta cell deficiency syndrome can be treated.

Typically, diabetes treatments include lifestyle modifications. Lifestyle modifications include changes in diet, exercise, nutraceutical and pharmaceutical regimens. In an embodiment, the methods of the invention further include lifestyle modifications. In another embodiment, the methods of the invention are applied without the need for lifestyle modifications.

Also provided are systems and apparatuses for stimulation of TRPV1 sensory neurons that innervate the endocrine pancreas.

The system can include an electrode lead or a multiple electrode lead array as disclosed elsewhere in this application.

The system can further include means for electrical neural stimulation in an open loop format. For example, the system can alert the subject to a change in glucose homeostasis, thereby allowing the subject to choose whether to initiate another electrical neural stimulation. The alert can be triggered by a sensor that detects a biomarker level achieving a specified threshold. In another embodiment, the device can be programmed to stimulate certain neural tissues at predetermined intervals, such as to maintain hormone levels at a certain concentration.

The system can further include means for electrical neural stimulation in a closed loop format. The system can include a feedback sensor. The feedback sensor can collect information on biomarker levels and transmit to a controller to compare measured levels to desired ranges. If outside the desired or threshold range, the feedback controller can initiate adjustments to parameter settings of the electrical stimulation. The efficacy of electrical stimulation can be evaluated so that the parameter settings can be adjusted to improve the response.

Figure 2:
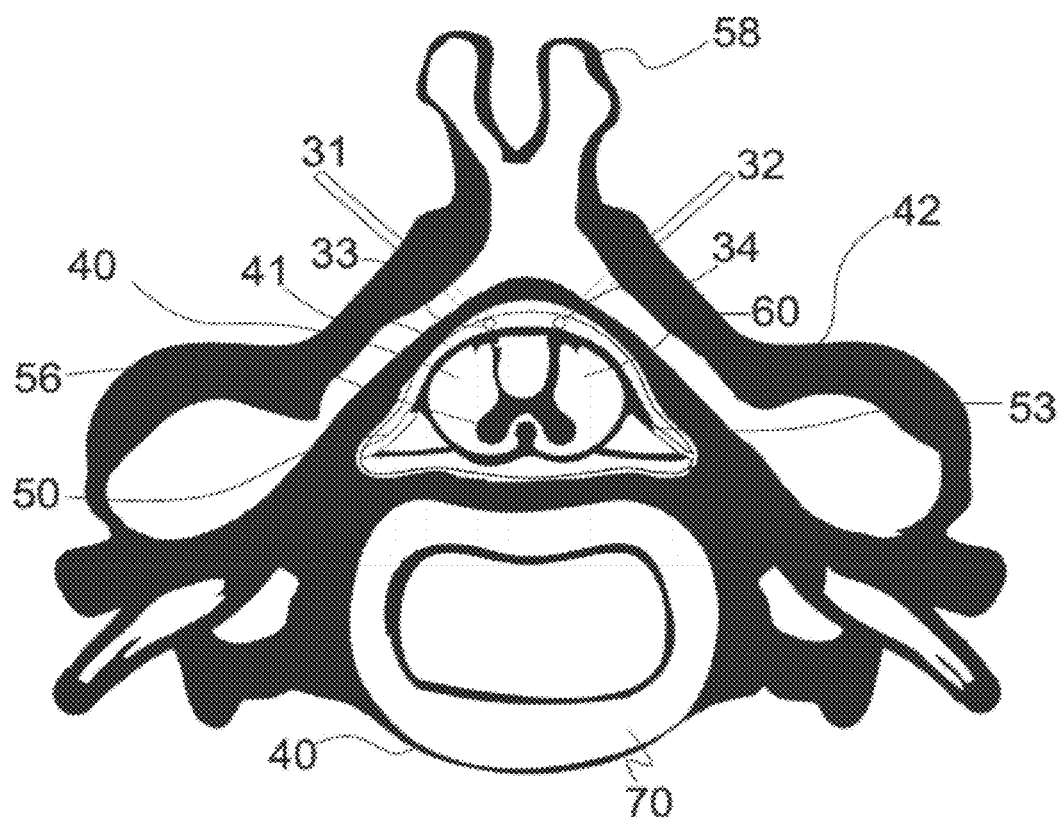
FIG. 2 shows a diagram of a cross-sectional view of a spinal column demonstrating a typical implantation position of the distal end of insulated electrode leads (31, 32), which terminate in electrodes (33, 34) within the epidural space (41).

FIG. 1 shows a schematic view of a subject 10 having an implant of a neural stimulation electrode lead to stimulate the targeted sensory nerves through epidural spinal cord stimulation. The system can employ an implantable 15 or external pulse generator 16 to produce a number of independent stimulation pulses which are sent to the spinal cord 20 by insulated lead 22 or wirelessly which has two or more electrodes 33 and 34 (FIG. 2). The implantable pulse generator 15 can have an internal battery and pulse-generating electrical components. The system can further comprise a radiofrequency antenna 18, which can be connected to an external programmer 12 by an extension 14. Alternatively, the pulse generator 16 can electrically process incoming radiofrequency signals from the antenna, and produce electrical pulses sequentially, without aid of a battery.

Electrodes can be placed near neural tissue. FIG. 2 is a diagram of a cross-sectional view of a subject spinal column 20 of a subject showing an embodiment where the implantation position of the distal end of insulated electrode leads 31 and 32, which terminate in electrodes 33 and 34 within the epidural space 41. Electrodes can be made of a platinum/iridium compound. The electrodes are shown relative to the subdural space 60 filled with cerebrospinal fluid (CSF), bony vertebral body 70, vertebral arch 42, and dura mater 43. The spinal cord includes gray matter 56 and white matter, for example, dorsal columns 40 and dorsolateral columns 58. At the dorsal tips of the gray matter are the dorsal roots 50 and 53, which are axons, originating from cell bodies in the dorsal root ganglia, 52 and 54. These same cell bodies have sensory endings in tissue, and their axons pass along spinal nerves 44 or 46. Stimulation pulses can be applied to at least one of electrodes 33 and 34 (which typically are cathodes); while at least one anode can be used for electrical return paths at other epidural space 41 locations. Models of electric fields with spinal cord stimulation (cf. Jan Holsheimer et al.), and clinical experience suggest that not only are axons in the dorsal columns 40 excited, but so are axons in the dorsal roots 50 and 53, and possibly also axons near to dorsal gray matter several millimeters away.

Figure 3:
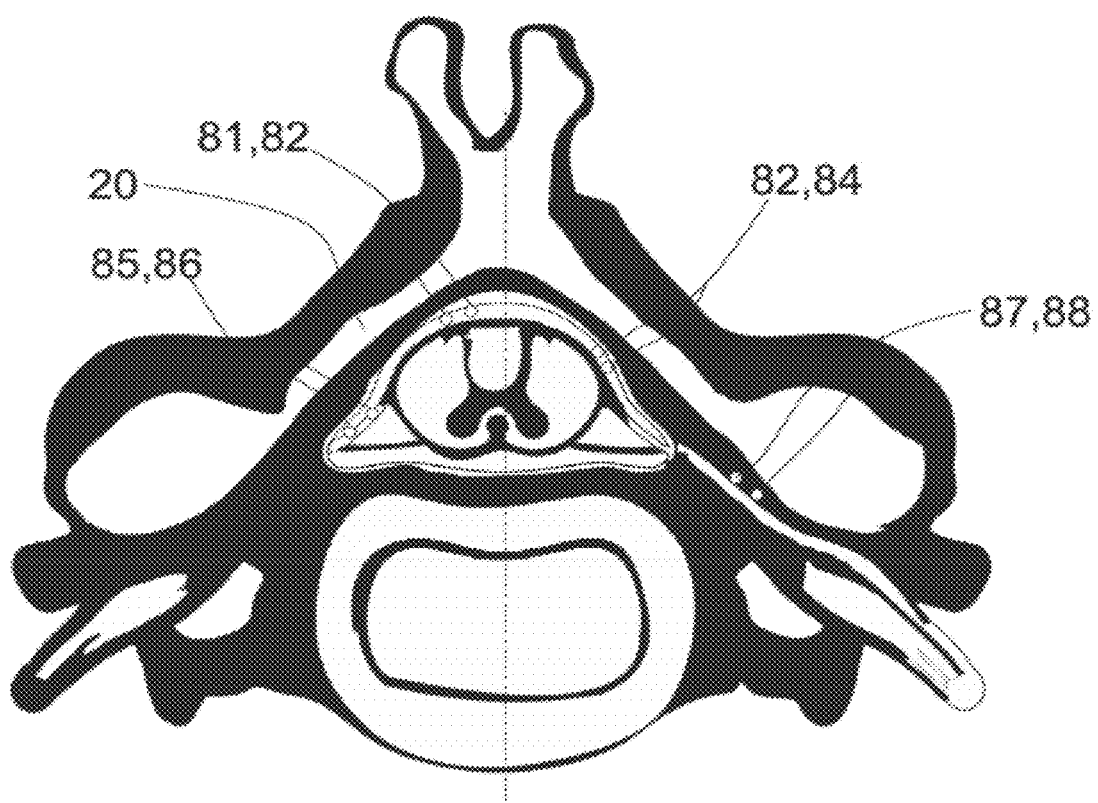
FIG. 3 shows a diagram of a cross-sectional view of a spinal column demonstrating potential electrode placement at four locations: dorsal columns (81, 82), dorsal roots and entry zone (83, 84), dorsal root ganglia (85, 86) and spinal nerves (87, 88).

Electrodes can be placed at one or more sites. FIG. 3 is a diagram of a cross-sectional view of a spinal column showing embodiments of electrode placement at different implantation sites to stimulate dorsal columns, dorsal roots and entry zone, dorsal root ganglia and/or spinal nerves. The diagram shows the spinal cord 20 of the subject relative to implantation sites of the electrodes which are useful to therapeutically control TRPV1 sensory neurons: 1) electrodes 81 and 82 for epidural spinal cord stimulation at segments T7 to L1 (sites with relatively significant proportions of branches of TRPV1 neurons innervating the pancreas); 2) electrodes 83 and 84 for dorsal root and dorsal root entry zone stimulation at segments T7 to L1; 3) electrodes 85 and 86 spinal nerve stimulation of nerves T7 to L1); 4) electrodes 87 and 88 for dorsal root ganglia stimulation of T7 to L1. Electrodes for therapeutic stimulation can also be placed at: 5) peripheral nerves innervating the pancreas; 6) abdominal nerves or their cutaneous branches; and/or 7) the surface of the pancreas. Two or more electrodes can be used, at least one of which is a cathode (negative) and at least one of which is an anode (positive). One or more of the electrodes used can be at spinal levels. In the case of anode(s), the electrode can be distant. Pulses may be current or voltage controlled. The pulses can be charge-balanced for safety. Electrodes can be placed in the epidural space, outside the dura, or subdurally. Electrodes may be placed nearby, outside the perineural sheath, or inside and along the nerve fibers of peripheral nerves.

Figure 4:
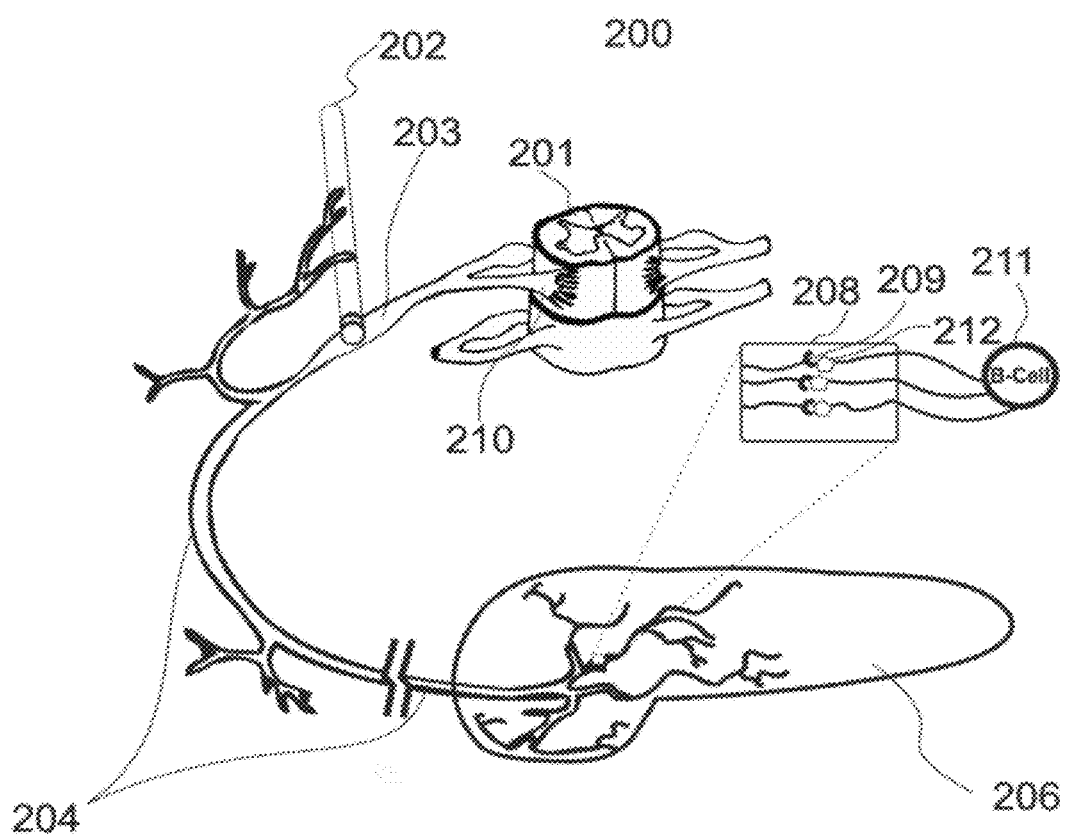
FIG. 4 is a diagram of a cross sectional pathway overview of a spinal column segment (201) at which an electrode lead (202) is placed to stimulate the dorsal root ganglia (203) and/or spinal nerves (210) from in the dermatome regions from spinal segments T7 to L1, which are sensory nerve fibers (204) that lead to the pancreas (206).

The electrodes can be placed near the dorsal root ganglia and/or the spinal nerves. FIG. 4 is a diagram of a cross sectional pathway overview 200 of an exemplary spinal column segment 201 showing positioning electrode lead 202 to stimulate the dorsal root ganglia 203 and/or spinal nerves 210 by placement perpendicularly with the nerve bundle leaving the particular dermatome. The electrode lead placement in FIG. 4 can stimulate TRPV1 sensory neurons via the dorsal root ganglia in the dermatome regions from spinal segments T7 to L1, which are sensory nerve fibers 204 that lead to the pancreas 206. Electrodes can also be placed at the: 1) peripheral nerves innervating the pancreas 204; 2) abdominal nerves or their cutaneous branches; and/or 3) the surface of the pancreas 206. While pairs of electrodes 202 are shown in FIG. 4, stimulation can be effected with two or more electrodes, at least one of which is a cathode (negative) and at least one of which is an anode (positive). One or more of the electrode leads used can be placed at different spinal levels or even distant in the case of anode(s). The sensory nerve terminals 208 contain TRPV1 and insulin receptors 209 that act on the release of certain neuropeptides, i.e. CGRP or respond to the presence of insulin 212. The neuropeptides act on the beta cell 211 and modulate the release or inhibition of insulin from the beta cell.

Figure 5:
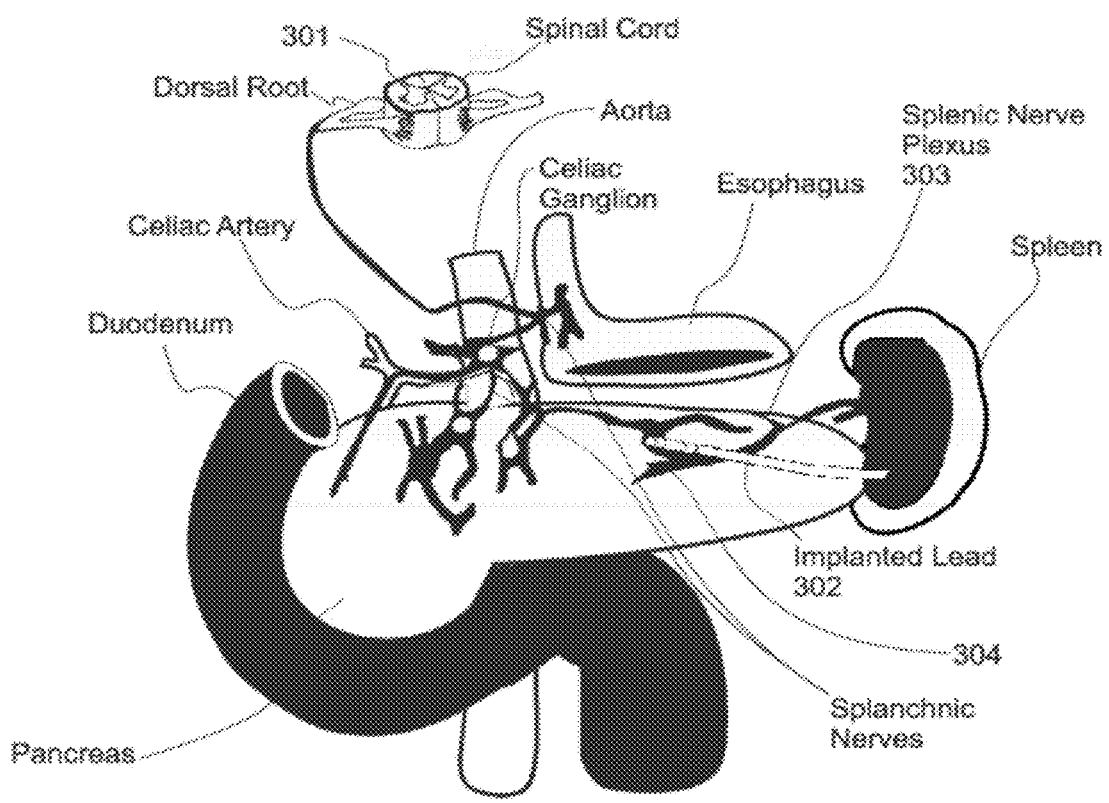
FIG. 5 shows a diagram of a cross sectional pathway overview, as in FIG. 4, but where the electrode lead (302) is placed to stimulate the splenic nerve.

The splenic nerve can be a site of electrode placement. FIG. 5 is an overview 300 of a subject spinal column segment 301 showing an electrode lead 302 placed to stimulate the splenic nerve 303 by placement in parallel with the nerve bundle 304.

Figure 6:
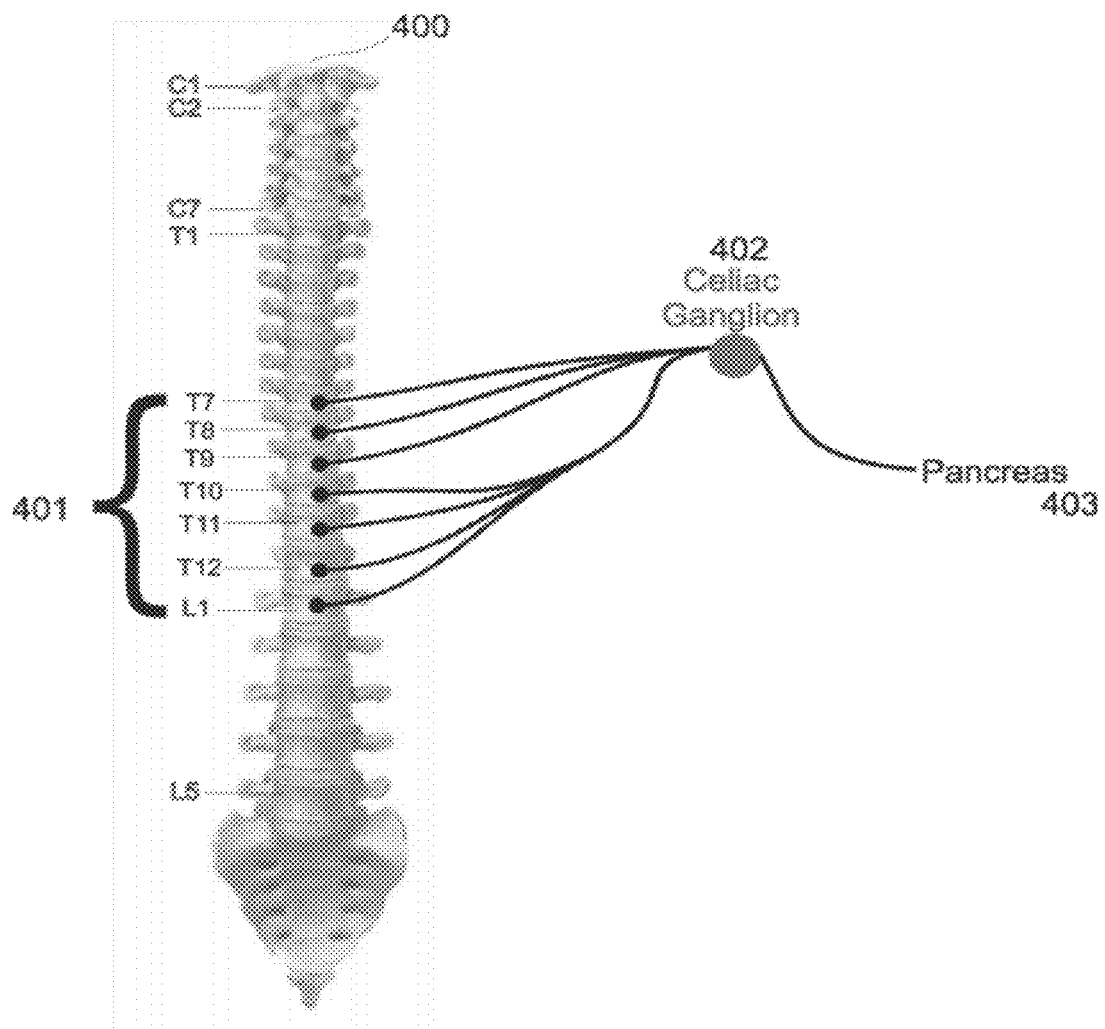
FIG. 6 shows a diagram of the various dermatome levels for nerve fibers to various tissues of the typical body of a subject (400). The viscera region is innervated by most of the dermatomes ranging from T7 to L1 (401).

FIG. 6 shows the various dermatome levels for nerve fibers to various tissue of the typical subject 400. The viscera region is innervated by most of the dermatomes ranging from T7 to L1 401.

Figure 7:
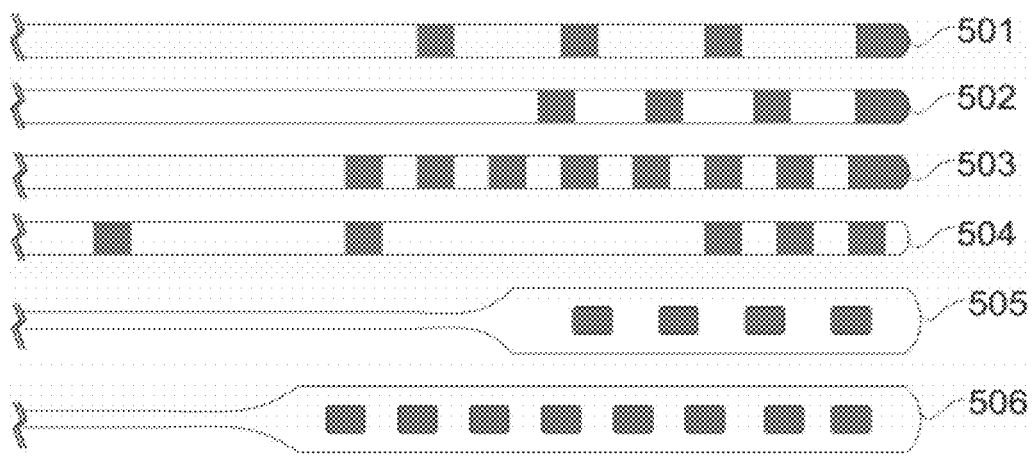
FIG. 7 shows various configurations for an electrode lead array. Shown are (a) four electrode leads with 3 mm spacing (501), (b) four electrode leads with spacing less than 3 mm (502), (c) 8 electrode leads with regular spacing on the lead (503) four electrode leads with spacing that includes electrodes at the tip, with remote anodes to create a wide area of volume conduction (504), (d) electrode pads (505) and embedded paddle electrode leads (506).

Electrode types and electrode spacing can be modified in suitable embodiments. FIG. 7 shows various optional configurations for the electrode lead array that can be placed in the epidural space, directly on the dorsal root ganglia, in the region of the splenic nerve, or other location along the neuronal pathway from the dorsal column to the pancreas originating from dermatomes in the region of T7 to L1. Typically, four electrode leads are sufficient for peripheral nerve stimulation placements 501. The spacing of these electrodes can be about 3 mm, as shown 501, however studies have shown that targeting of the nerve bundle can be improved by electrode spacing that is less than 3 mm 502. In other embodiments, such as for greater range of coverage in epidural space placements, leads with 8 electrodes 503 or more can be used to cross over multiple dermatome levels. In other embodiments 504, spacing can include electrodes at the tip, with remote anodes to create a wide area of volume conduction. In yet another embodiment, the electrode pads can be placed in a configuration that eliminates the 360 degree electrode wrapping around the lead 503 and places the electrodes embedded in a lead assembly where placement must be manually inserted to lie against the spinal column within the lead unilateral volume conduction area 505. Embedded paddle electrode leads can have a multitude of electrode pads 506.

Figure 8:
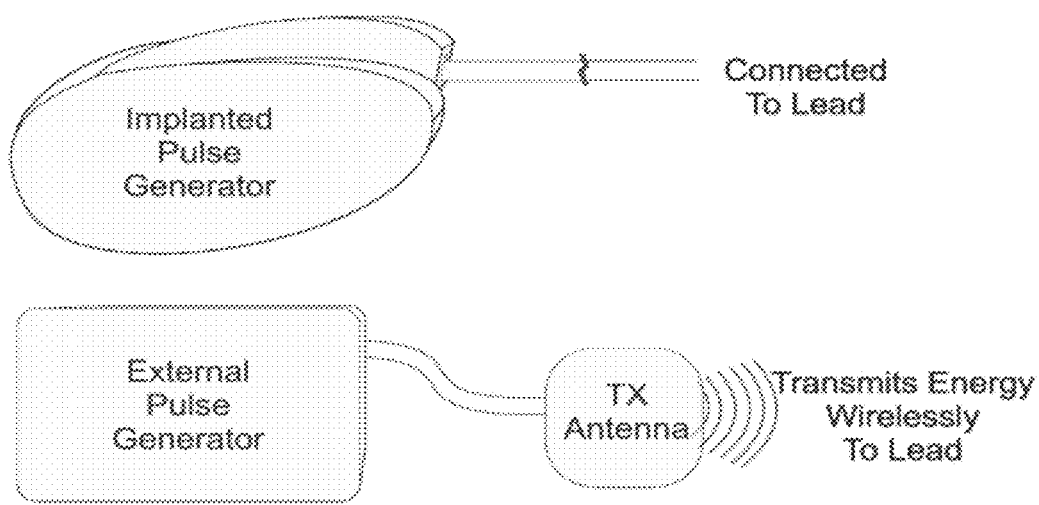
FIG. 8 shows a neural stimulator device powered by an implanted pulse generator (IPG).

In some embodiments, the invention further comprises an implanted pulse generator (IPG) that can be used for open- or closed-loop feedback. FIG. 8 is a diagram showing an IPG and an external pulse generator system. The IPG can be located subcutaneously in the abdomen or lower back region and tunneled by extension wire to the electrode lead at the therapeutic treatment area. Alternatively, pulse information can be received for this treatment protocol by an external pulse generator sending information to an imbedded antenna receiver which interprets and correlates the instruction set to provide the electrode lead with the appropriate therapeutic parameter sets.

The system and apparatus can further include a controller. The controller can generate excitatory or inhibitory electrical stimulation to TRPV1 sensory neurons to alleviate the imbalance between insulin production from the β-cell-CGRP release. The controller can communicate with one or more sensors to detect biomarker levels as disclosed herein.

The controller can comprise one or more transmitters and receivers in communication with sensors and the electrical stimulation device such as the pulse generator. The controller can send the signals to increase or decrease stimulation until glucose homeostasis is achieved. The stimulus parameters include, without limitation, amplitude, pulse duration, duty cycle, pulse width/frequency, and polarity of electrodes on the lead. The controller can include a microprocessor that can instruct the system to produce an exciting or inhibiting stimulation signal or to cease electrical stimulation. The microprocessor can be programmed with pre-selected stimulus parameters. The receivers receive signals from the sensors, process signals to be analyzed by the controller and store the signals in a data storage and/or pre-processor area, such as a dynamic random access memory (DRAM). Sensors sense various biomarker levels to determine, for example, whether there has been sufficient glucose homeostasis control in the neuroendocrine system.

The controller can be an external device or an implantable device. In certain embodiments, it can provide signals to a subject who is experiencing an unexpected event. The controller can be programmed for either automatic or manual operation. The controller can have one or more conventional glucose sensors. Upon detection of a hormonal irregularity, the controller can automatically begin treatment of the subject by regulating hormone levels through electrical stimulation. In another embodiment, the subject can manually activate the controller. The activation can begin or adjust regulation of CGRP levels. The activation can regulate insulin homeostasis. A positive physiological response, e.g. a physiological response that trends to the "normal" range, can be used as an indication that the electrical stimulation is effective in producing glucose homeostasis.

Figure 9:
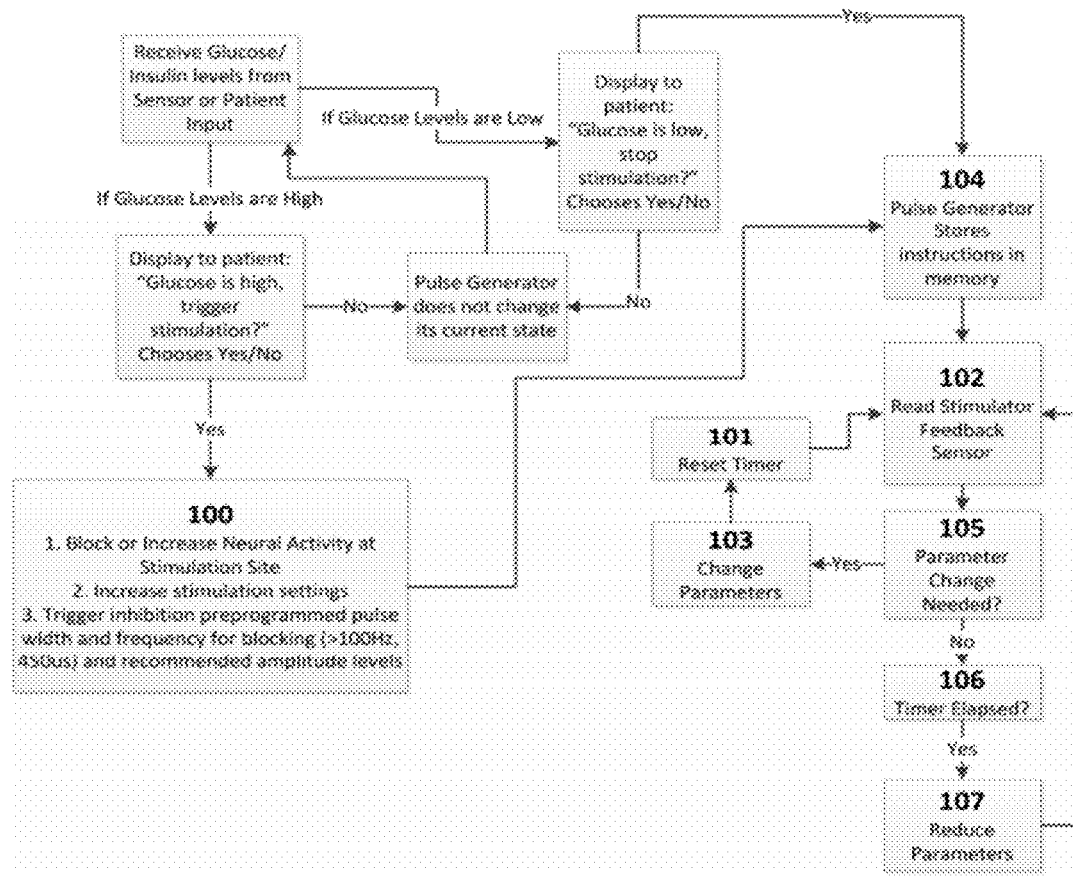
FIG. 9 is a schematic diagram of a closed-loop controller, which includes sensing of physiological parameters and adjusting stimulation parameters.

In some embodiments, the invention further comprises a closed-loop controller. FIG. 9 is a schematic diagram of a closed-loop controller, which includes sensing of biomarker levels and adjusting stimulation parameters. The closed-loop controller generates excitatory or inhibitory electrical stimulation to TRPV1 neurons alleviating the imbalance between insulin production from the β-cell and CGRP production. The controller utilizes one or more sensors to detect the biomarker level. The controller compares sensed biomarker levels (data) 102 to stored historic or normative levels 104, and adjusts the stimulation output accordingly. Physiological normative data, past data from this subject, and ranges of stimulation parameters can be saved in storage element 100. Once sensed data is acquired 102, a decision can be made 105, optionally based on priorities, whether stimulation must be initiated or altered to affect this parameter. The controller can effect changes to parameters or to anatomical locations of stimulation as required 103. The controller can effect these changes independent of altering the timing element 101 of the electrical stimulation. If the decision to change a parameter or location of stimulation is negative, the timer will be checked 106, and either the timer will be reset, or parameters of stimulation in general can be reduced 107, but not below a priori limits. The controller can consult with two or more sensed physiological values before making decisions.

Example 1

The Biological Feedback Loop Between SSNF and Beta Cells

Figure 10:
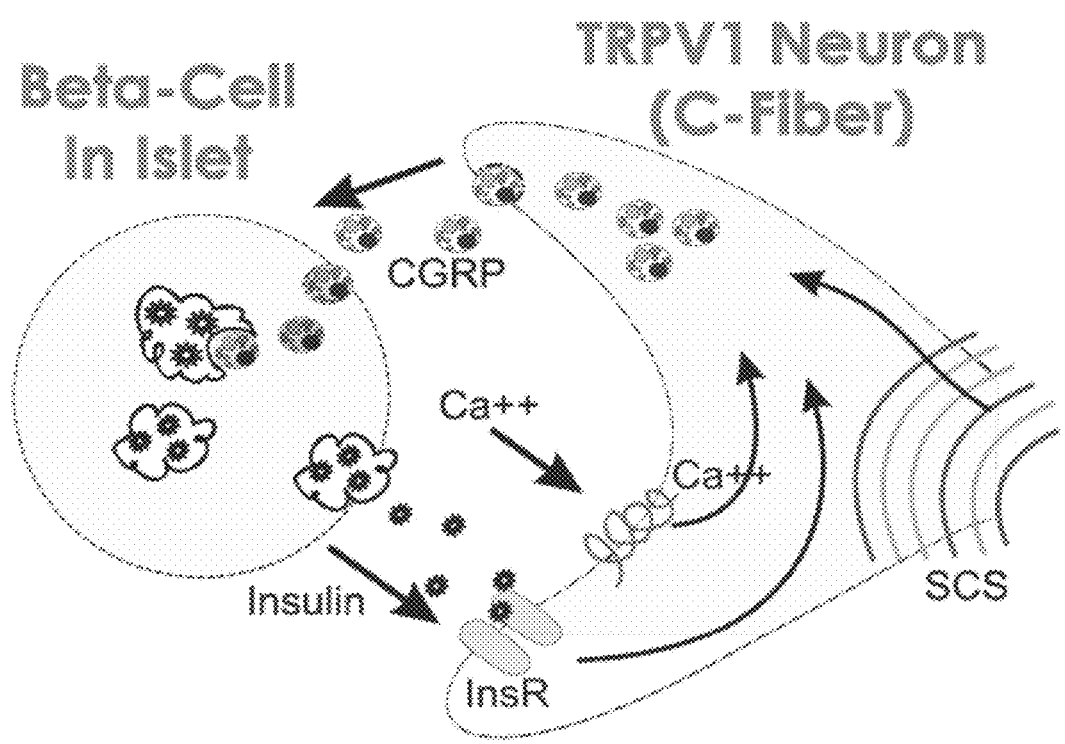
FIG. 10 shows a cartoon of the feedback loop between a small sensory nerve fiber (SSNF) ending containing TRPV1 sensory neurons (e.g., C-fibers) secreting neurogenic peptides and beta cells stimulating insulin action.

The biological feedback loop between a small sensory nerve fiber (SSNF) ending containing TRPV1 sensory neurons (e.g. C-fibers) secreting neuropeptides and beta cells stimulating insulin action can be controlled by electrical stimulation. FIG. 10 shows a feedback diagram of a SSNF ending containing TRPV1 sensory neurons (e.g., C-fibers) when modulated by electrical neural stimulation techniques by methods described in this invention act on the nerve bundles dorsal root ganglia through volume conduction from a dorsal column placement of an electrode lead, or other methods of sensory nerve stimulation described herein. The neuropeptide CGRP, among others, are released from the activated TRPV1 sensory neuron terminal. The released neuropeptides act on the beta cell stimulating insulin action through an inflammatory response action.

Subjects treated with spinal cord stimulation using excitatory protocols described herein show a marked effect (i.e., an increase in) on insulin production. This closed loop system can also be inhibited to cut off the production of insulin from the beta cell. Insulin released from the beta cell acts on the insulin receptor located on the TRPV1 sensory neuron terminal. The influx of insulin into the sensory nerve cells up regulates the TRPV1 receptor channel and an influx of calcium enters the cell, which leads to the release of CGRP neuropeptide from the cell, closing the loop to act on the beta cell invoking insulin release. Electrical neural stimulation parameters are set in this invention to both stimulate the cycle of release of insulin and/or inhibit the cycle with blocking parameter settings.

Example 2

Placement of Epidural Neural Stimulator

A spinal cord stimulator (SCS) is a medical device typically used for the treatment of chronic pain, which usually includes an implantable lead, a pulse generator (implanted or external) and a power source as shown in FIG. 1. Wired SCS devices introduce an implantable lead containing a number of electrodes into the epidural space, as well as an extension cord to an implantable pulse generator (IPG). These IPGs can either contain a battery pack or a radio frequency (RF) receiver and are typically placed under the skin around the buttocks or hip area. The diabetic subject would have SCS leads placed at a medical facility bilaterally. The subject lays down on a flat surface with their back facing upwards. Typically, a 14-gauge Tuohy needle (2.1 mm diameter or less) is inserted into the back and is carefully navigated upwards into the epidural space of the spinal cord with the aid of a fluoroscope or other imaging device. Once the Tuohy needle is located properly, a guide wire is pushed through the lumen of the needle in order to safely move tissue to the side creating a pathway for the lead. The guide wire is removed, and then the SCS lead is advanced through the interior of the needle. The lead is advanced up into the epidural space until the electrodes are near the nerve branches that correspond to the location of the dermatomes that innervate the pancreas small sensory nerve fibers.

Stimulating electrodes incorporated into a lead can be placed at the 9th to 11th thoracic (T9-T11) vertebrae directly through various implantation orthopedic techniques. The implantable stimulation electrodes are made of inert materials, such as platinum-iridium. The leads are made from a biocompatible polyurethane or silicone and may contain a silicon microelectronic chip. When energized, the implanted device produces small waveform pulses of a current to excite or inhibit a release of neural transmitters, depending on the parameter settings of frequency and pulse width. The lead can be secured in place with a steristrip or a monofilament absorbable (Monocryl) suture to anchor device.

SCS can be applied at the epidural surface of T9-T11 vertebrae spinal location in the center of the cord for example, or bilaterally on either side of the cord. SCS has been shown to increase vasodilation in the skin through release of CGRP from the afferent fibers in the dorsal roots (Tanaka 2004). Muscle twitch threshold and threshold under epidural stimulation was determined. Continuous epidural electrical stimulation can be delivered at 5 Hz, for insulin production or 100 Hz, for insulin inhibition at various pulse durations. The stimulation intensity ranges from 100 µA to a maximum of 10 mA.

Example 3

Electrical Stimulation Regulates Insulin Activity in Diabetics

SCS-induced modulation of SSNFs leads to enhanced insulin action and release. This can occur as a result of improved SSNF function and restoration of insulin receptor regulation. Outcome measures include the Oral Glucose Tolerance Test (OGTT) and a Homeostasis Model Assessment of Insulin Sensitivity (HOMA) analysis. Oral Glucose Tolerance Test (OGTT) is a widely used procedure that was originally developed to classify carbohydrate tolerance. The OGTT requires the subject to be fasting overnight. A plasma sample is then drawn to determine baseline values for glucose and insulin. Following an oral glucose load (usually by swallowing 75 grams of dextrose), the glucose and insulin in blood plasma samples are measured at specific times, such as 30 minutes and 120 minutes (Weyer 1999). The test indicates the ability (also called tolerance) of pancreatic β-cells to respond to glucose stimulation by secreting sufficient amounts of insulin to maintain glucose homeostasis.

Using the OGTT, other indices of β-cell function can be measured: $\Delta$ Ins/$\Delta$Gluc at 30 minutes is reduced ~6-fold in early diabetes and the glucose area under the curve (AUC) is raised ~2-fold in early diabetes, reflecting impaired modulation of glucose after a glucose load or glucose intolerance. The gold standard test for Insulin Resistance (IR) is the euglycemic hyperinsulinemic clamp, a procedure that is technically complex and not practical for clinical research particularly with large population samples. The Homeostasis Model Assessment of Insulin Sensitivity (HOMA) is used to analyze the results (Stumvoll et al, 2000; Haffner et al, 1997). It is derived from the OGTT and is calculated as [fasting insulin (µU/ml)×[fasting glucose (mmol/L)]/22.5. The HOMA has a range of ~0.2-15. The correlation coefficient with the clamp is about 0.75, suggesting a strong correlation. Higher scores are associated with glucose intolerance, progression to diabetes, the metabolic syndrome, and cardiovascular disease. For the HOMA scale, the highest quartile for IR among a non-diabetic population is 3.0; thus we will use >3.0 values to depict IR in our population.

Subjects that are treated with SCS use the system a minimum of three times daily to elicit changes in pancreatic function. The treatment time intervals are determined by each individual subject's use of the device and eating patterns. Durations for each treatment session are at least 15 minutes of SCS 3 times daily. The subject uses the stimulator for a prescribed period of time each day, for example 15 minutes three times daily, or 30 minutes six times daily. As much as possible these three 'treatments' should occur at the same times each day. A Daily Stimulation Log is used to record treatment times and length for the stimulation. After ten days of treatment, subject logs are reviewed by the endocrinologist along with the HOMA analysis to mark the impact of the SCS treatment on the subject's overall systemic glucose levels.

Before the end of the first month of SCS treatment, the subject fasts 9-12 hours overnight before a final office for a series of blood draws to determine the effects of the SCS treatment. At start, in a fasting state a blood sample is taken for baseline glucose and insulin values for OGTT. The subject is given 75 g of dextrose mixture to ingest (glucose load). At 30 minutes a second blood sample is taken for glucose and insulin values. At 120 minutes a third blood sample is taken for glucose and insulin values. Two weeks later the subject will fast overnight before a visit to the site for about 3 hours during which they will again have 3 blood draws. At start, in a fasting state a blood sample is taken for Fructosamine and baseline glucose and insulin values for OGTT. The subject then ingests 75 g dextrose mixture (glucose load). At 30 minutes a second blood sample is taken for glucose and insulin values. At 120 minutes a third blood sample is taken for glucose and insulin values.

Again after at least two weeks, the subject will fast overnight before a visit for about 3 hours during which they will again have 3 blood draws, plus the LDF abdominal blood flow analysis. At start, in a fasting state a blood sample is taken for Fructosamine and baseline glucose and insulin values for OGTT. The subject then ingests 75 g dextrose mixture (glucose load). At 30 minutes a second blood sample is taken for glucose and insulin values. At 120 minutes a third blood sample is taken for glucose and insulin values. LDF Abdominal blood flow is again recorded. SCS treatment is shown to elicit an insulin action from the beta cell after treatments of 15-minute duration.

Example 4

Electrical Stimulation Regulates Abdominal Blood Flow

Figure 11:
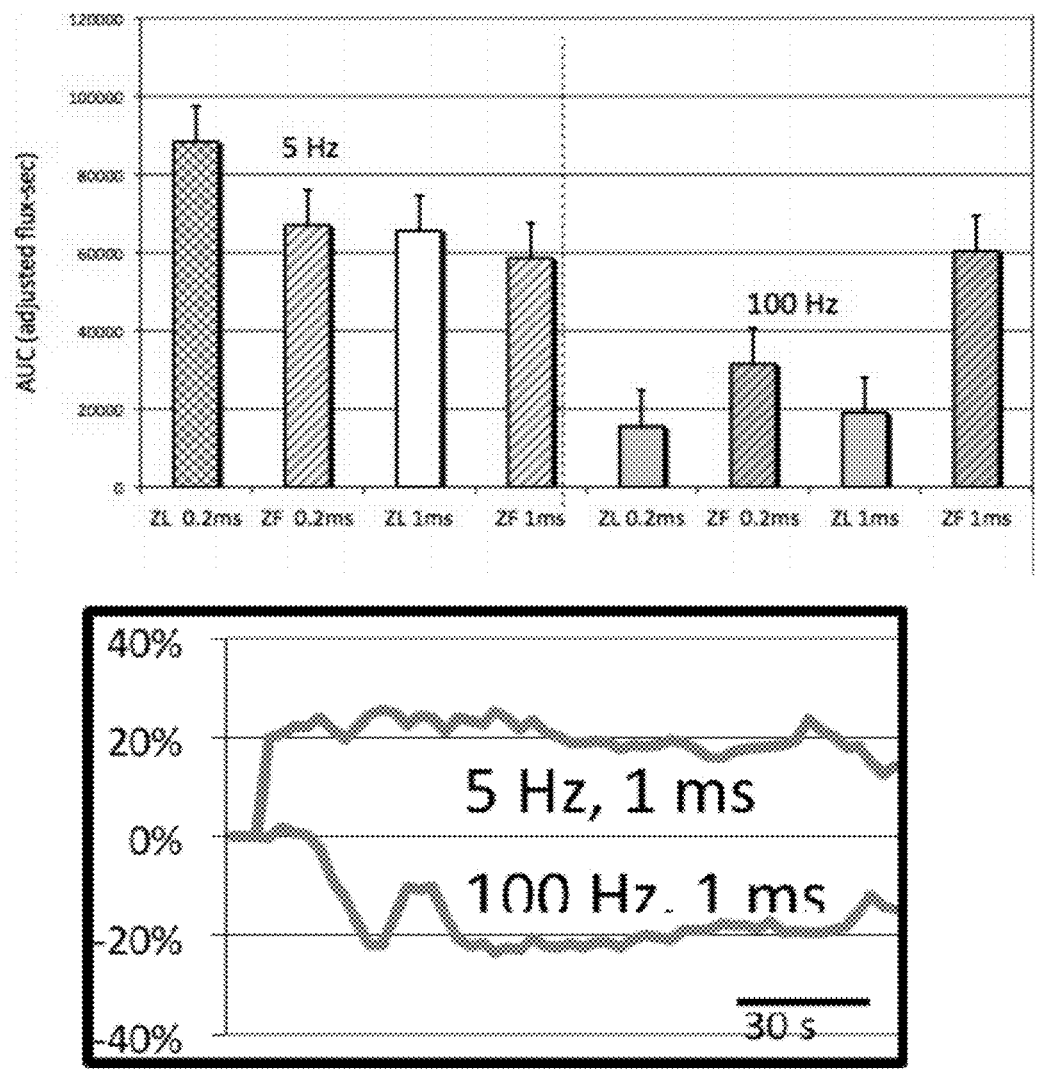
FIG. 11 shows the effect of neural stimulation upon abdominal blood flow in the rat model: (A, top panel) area under the curve (AUC) in Zucker Lean (ZL) and Zucker Fatty (ZF) rats at the indicated frequencies (5 Hz or 100 Hz) and pulse durations (0.2 ms and 1 ms); (B, bottom panel) time course of spinal cord stimulation of rats at the indicated frequencies (5 Hz, increase in blood flow, or 100 Hz, decrease in blood flow) and pulse duration of 1 ms.

Zucker Lean and Zucker Fatty rats are subjected to intermediate 90 second 5 Hz (exciting) and 100 Hz (blocking) stimulation at 0.2 microseconds or one millisecond pulse durations as indicated in FIG. 11. Top panel, the four left bars are 5 Hz and the right four bars are 100 Hz. Abdominal blood flow is analyzed by a laser Doppler (Moor Instruments) measuring the area under the curve (AUC) FIG. 11. The following observations are made: (1) spinal cord stimulation causes higher abdominal skin blood flow at 5 Hz rather than 100 Hz and (2) Zucker fatty rats do not exhibit negative blood flow at inhibitory frequencies of 100 Hz suggesting that these animals do in fact have a serious impairment of sympathetic nerve fibers. The magnitude of blood flow in the obese rats is only minimally decreased, perhaps due to the relatively young age of the rats and/or to residual vasodilatory molecules that are released by spinal cord stimulation.

Abdominal Blood Flow (ABF) tests are used to compare different pulse durations in order to select the one that maximizes blood flow. To optimize the stimulation, blood flow is used as an output measure at the abdomen because the same sensory nerve fibers innervate both the pancreas and the abdomen. The SCS system for example would be turned on twice for a certain period of time at least 2 to 3 hours after a meal, i.e., for 15 minutes with a 15-minute rest interval between treatments. During the stimulation session, changes in abdominal blood values at the abdomen will be recorded using a surface Laser Doppler Flowmetry (LDF) (Moor Inst Co. Devon, England). The stimulation parameters typically will be set at a frequency of 5 Hz and a pulse duration at 0.2 ms. Intensity at or near motor threshold of the abdominal muscles will be assessed by recording surface electromyography (SEMG) signals of less than 200 µV from the upper abdominal muscles. Blood flow response output measurements include peak values, area under curve, and correlation curves to EMG recordings of voltage levels required to generate a muscle action potential. Successful treatment candidates will exhibit an increase of at least 10% or more (above baseline resting values) in blood flow measured 60 seconds prior to stimulation on at least one side of the abdomen.

Local blood flow can be measured in the dorsal skin with a laser Doppler blood flow meter as a diagnostic tool to ensure vasodilation is being achieved by the stimulation protocols Skin sites were marked out on the dorsal skin according to a balanced site pattern with two sites for each measurement on the right side of the abdomen corresponding to the location of the pancreas. Laser probes are adhered to the skin with an adhesive attached via a laser probe holder perpendicular to the abdomen skin. The laser Doppler flow meter is set at 5 Hz at a gain of 10. The blood flow readings can be taken sequentially at each site at 2-second intervals. Both ipsilateral and contralateral data can be analyzed.

The raw blood flow flux measurement data and the area under the curve can be calculated to express results as a percentage of change in blood flow as observed from the abdomen skin innervated by SCS. Measurements to be evaluated include the percent change from baseline blood flow values. The system measures (1) dose-dependent abdominal blood flow and vascular resistance responses during SCS with current patterns blood flow at the two sites; (2) sustained blood flow at a selected sub-threshold level 80-90% of motor threshold for the abdominal muscles as activated by SCS prior to and following multiple epochs of stimulation; and (3) testing timelines till the depletion of CGRP by blood flow.

What is claimed is:

1. A method for treating a metabolic disease or disorder in a human subject suffering from said metabolic disease or disorder by inhibiting secretion of calcitonin gene-related peptide (CGRP) from one or more C-afferent sensory nerve fibers, comprising:
    applying, via a pulse generator in operable communication with an implantable lead, an electrical impulse to one or more C-afferent sensory nerve fibers innervating pancreatic beta cells in the subject, the electrical impulse configured to have a frequency ranging from 60 to 10,000 Hz and further configured to inhibit the secretion of CGRP from the one or more C-afferent sensory nerve fibers to treat the metabolic disease/disorder.

2. The method of claim 1 wherein the applying step is carried out by applying the electrical impulse using one or more electrodes or pairs thereof.

3. The method of claim 2 in which said one or more electrodes or pairs thereof are contained in an implantable or percutaneous device, the method further comprising positioning the implantable or percutaneous device in said subject at a target site proximal to nerve tissue to be stimulated, wherein the target site includes one or more of the following: proximal to epidural spinal cord column at any vertebral segment from T7 to L1, dorsal root or dorsal root entry zone at any vertebral segments from T7 to L1, spinal nerve bundles leaving at any vertebral segments from T7 to L1, dorsal root ganglia bundles leaving at any vertebral segments from T7 to L1, peripheral nerves innervating endocrine pancreas beta cells, abdominal nerves or their cutaneous branches, a surface of endocrine pancreas, or combinations thereof.

4. The method of claim 3 in which said one or more electrodes or pairs thereof are placed ipsilaterally or bilaterally.

5. The method of claim 2 wherein the applying step is carried out via two or more electrode pairs contained in one or more implantable leads or percutaneous devices and said applying step is carried out simultaneously or sequentially.

6. The method of claim 2 further comprising wirelessly transmitting an input signal from a location outside of a body of the subject to an implantable or percutaneous device comprising the one or more electrodes or pairs thereof and converting the input signal into the electrical impulse at a target site within the body of the subject.

7. The method of claim 6 wherein the input signal comprises energy to provide power to the implantable or percutaneous device.

8. The method of claim 1 wherein the electrical impulse has a pulse width from about 450 to 1000 microseconds and a power amplitude from 0.2 to 14 Volts (V) or 0.1 to 20 milliamps (mA).

9. The method of claim 1 wherein said metabolic disease or disorder comprises diabetes mellitus.

10. The method of claim 1 wherein said metabolic disease or disorder comprises Type I diabetes.

11. The method of claim 1 wherein said metabolic disease or disorder comprises Type II diabetes.

12. The method of claim 1 wherein said metabolic disease or disorder comprises diabetes insipidus.

13. The method of claim 1 further comprising determining a level of a biomarker in the subject and applying additional electrical impulses to the one or more C-afferent sensory nerves as a function of the level of the biomarker.

14. The method of claim 13 in which said subject effects the step of applying additional electrical impulses.

15. The method of claim 13 in which the step of applying additional electrical impulses is effected automatically.

16. The method of claim 13 in which said biomarker is selected from the group consisting of insulin, glucose, CGRP, abdominal skin blood flow, abdominal skin temperature and abdominal muscle activity.

17. The method of claim 16 in which:
 a. said biomarker is insulin and,
  i. said subject is a male subject and said level is below about 8.8 μIU/mL or said subject is a female subject and said level is below about 8.4 μIU/mL; and the electrical impulse is configured to excite said C-afferent sensory nerve fibers innervating pancreatic beta cells; or
  ii. said subject is a male subject and said level is above about 8.8 μIU/mL or said subject is a female subject and said level is above about 8.4 μIU/mL; and the electrical impulse is configured to inhibit said C-afferent sensory nerve fibers innervating pancreatic beta cells; or,
 b. said biomarker is glucose; and
  i. said level is above about 120 mg/dL and the electrical impulse is configured to excite said C-afferent sensory nerve fibers innervating pancreatic beta cells; or
  ii. said level is below about 100 mg/dL and the electrical impulse is configured to inhibit said C-afferent sensory nerve fibers innervating pancreatic beta cells.

18. The method of claim 13 in which said biomarker is selected from the group consisting of H1Ac and inflammatory cytokines.

19. A system adapted for treating a metabolic disease or disorder in a human subject suffering form said metabolic disease or disorder by inhibiting secretion of CGRP from one or more C-afferent sensory nerve fibers, comprising:
 a power supply configured to generate an electrical impulse having a frequency of 60 Hz to 10,000 Hz; and
 an implantable lead configured to apply the electrical impulse configured to stimulate C-afferent sensory nerve fibers innervating pancreatic beta cells in a subject, wherein the electrical impulse is configured to inhibit a secretion of CGRP from said C-afferent sensory nerve fibers.

20. The system of claim 19 wherein the implantable lead is configured for positioning adjacent to or near a dorsal root ganglion, splenic nerve, or dorsal column.

21. The system of claim 19 wherein the power supply is configured to generate the electrical impulse in an open loop format.

22. The system of claim 21 wherein the power supply is configured to generate the electrical impulse at predetermined intervals.

23. The system of claim 21 wherein the power supply is configured to generate the electrical impulse in a manner to maintain hormone levels at a predetermined concentration.

24. The system of claim 21 in which the open loop format comprises alerting the subject to a change in glucose homeostasis.

25. The system of claim 21 further comprising a sensor for detecting a biomarker in the subject and wherein the subject is alerted when the biomarker level achieves a threshold level.

26. The system of claim 25 further comprising a controller coupled to the power supply and configured to compare detected biomarker levels to at least one predetermined range, and the sensor is configured to transmit information about the biomarker level to the controller.

27. The system of claim 25 wherein the controller is further configured to compare the biomarker level to an historic or normative level and adjust the electrical impulse based on the comparison.

28. The system of claim 26 wherein the controller is further configured to initiate adjustments to parameter settings of the electrical impulse.

29. The system of claim 28 wherein the controller is further configured to evaluate the efficacy of the electrical impulse so that the parameter settings can be adjusted.

30. The system of claim 28 wherein the controller is implantable in the subject.

31. The system of claim 21 further comprising a controller for allowing the subject to initiate generation of the electrical impulse.

32. The system of claim 19 wherein the power supply is configured to generate the electrical impulse in a closed loop format.

33. The system of claim 19 wherein the implantable lead further comprises an antenna for receiving incoming signals from an external programmer.

34. The system of claim 33 wherein the power supply is configured to electrically process the incoming signals and produce the electrical impulse sequentially without the aid of a battery.

35. The system of claim 19 wherein the electrical impulse is charge-balanced.

36. The system of claim 19 wherein the electrical impulse is generated automatically.

37. An apparatus adapted for inhibiting secretion of CGRP from one or more C-afferent sensory nerve fibers comprising:
 a sensor configured to detect a biomarker level;
 a pulse generator configured to produce electrical stimulation as a function of the biomarker level; and
 an electrode lead or a multiple electrode array; in which the pulse generator applies the electrical stimulation to the electrode lead or multiple electrode array; and in which the electrode lead or multiple electrode array comprises an electrode to apply the electrical stimulation configured to stimulate C-afferent sensory nerve fibers innervating pancreatic beta cells in a subject, in which said electrical stimulation has a frequency of 60 Hz to 10,000 Hz and is configured to inhibit a secretion of from said C-afferent sensory nerve fibers.

38. The apparatus of claim 37 in which the electrode lead or multiple electrode array is configured for positioning at or near a dorsal root ganglion, splenic nerve, or dorsal column.

39. The apparatus of claim 37 in which the pulse generator is implantable in the subject.

40. The apparatus of claim 37 in which the apparatus further comprises a radio frequency antenna for receiving incoming signals from an external programmer.

41. The apparatus of claim 37 in which the biomarker is any one or more of insulin, glucose, calcitonin gene-related peptide, abdominal skin blood flow, abdominal skin temperature and abdominal muscle electrical activity.

* * * * *

UNITED STATES PATENT AND TRADEMARK OFFICE
CERTIFICATE OF CORRECTION

PATENT NO. : 8,903,501 B2
APPLICATION NO. : 13/436293
DATED : December 2, 2014
INVENTOR(S) : Laura Tyler Perryman Page 1 of 1

It is certified that error appears in the above-identified patent and that said Letters Patent is hereby corrected as shown below:

In the Claims

In claim 13, column 17, lines 27-28, delete "sensory nerves" and insert -- sensory nerve fibers --, therefor.

In claim 19, column 17, line 60, delete "form" and insert -- from --, therefor.

Signed and Sealed this
Twenty-third Day of February, 2016

Michelle K. Lee
*Director of the United States Patent and Trademark Office*